United States Patent [19]

Mandy et al.

[11] 4,075,353

[45] Feb. 21, 1978

[54] PROCESS FOR THE TREATMENT OF ACARID SKIN INFECTIONS IN ANIMALS

[75] Inventors: Stephen H. Mandy, Coconut Grove; William D. Thompson, Miami, both of Fla.

[73] Assignee: Dermatologics for Veterinary Medicine, Inc., Miami, Fla.

[21] Appl. No.: 694,356

[22] Filed: June 9, 1976

[51] Int. Cl.$^2$ .......................................... A61K 31/075
[52] U.S. Cl. .................................................. 424/338
[58] Field of Search ........................................ 424/338

[56] References Cited

U.S. PATENT DOCUMENTS

| 3,530,217 | 9/1970 | White et al. | 424/338 |
| 3,535,422 | 10/1970 | Cox et al. | 424/338 |

OTHER PUBLICATIONS

Cebrian – Chem. Abst., vol. 76, (1972), p. 103763z.

*Primary Examiner*—Sam Rosen
*Attorney, Agent, or Firm*—Morgan, Finnegan, Pine, Foley & Lee

[57] ABSTRACT

A process is provided for treating skin infections, caused by parasites, bacteria and/or fungal pathogens in animals, said process comprising topically administering a therapeutic amount of benzoyl peroxide to the afflicted animal.

31 Claims, No Drawings

PROCESS FOR THE TREATMENT OF ACARID SKIN INFECTIONS IN ANIMALS

BACKGROUND OF THE INVENTION

This invention relates to the treatment of microbial cutaneous infections in animals and more particularly to the treatment of cutaneous infections, caused by parasites, bacteria and/or fungi in animals.

Skin infections in animals, such as horses, dogs, cats, cows, sheep and the like, which are caused by parasites, bacteria and fungi are very common. For example, a particularly common skin infection in animals is mange. Mange is caused by the presence of a burrowing parasitic mite, usually Sarcoptes or Chorioptes. Demodectic mange, which occurs primarily in domestic animals, and most severely in dogs, is an infection of the hair follicles and sebaceous glands, and is also caused by a burrowing parasitic mite, namely, Demodex folliculorum. This disease often results in severe dermatitis, especially in dogs, involving the entire body in some cases, and causes severe discomfort to the animal. Bacterial infections in animals may be secondary to an underlying dermatitis, such as in pyoderma, or may be the primary problem, as in impetigo.

In general, microbial skin infections are treated by topically applying a therapeutic agent to the infected animal. The most common therapeutic agent used in the past for treating mange and other related skin infectiions in animals is O,O-dimethyl O-(2,4,5-trichlorophenyl) phosphorothioate, commonly known as Ronnel, an insecticide belonging to the organophosphates. Bacterial and fungal infections are often treated with systemic antibiotics and/or topical antibiotics which are specific for a given organism.

While some of these prior art therapeutic agents do provide some relief for the animal, their overall effectiveness and ability to provide adequate results in a relatively short period of time, especially in the treatment of mange and particularly demodectic mange in dogs, leaves much to be desired. One particular problem with prior art therapeutic agents, especially Ronnel, is the serious hazard of poisoning which can be concomitant with its use.

SUMMARY OF THE INVENTION

Accordingly, it is one object of the present invention to provide a novel process for the treatment of microbial skin infections in animals.

Another object of this invention is to provide a process for the treatment of microbial skin infections in animals which is more effective and has less deleterious side effects than treatments known heretofore.

Still another object of this invention is to provide a novel process for the treatment of skin infections caused by parasites, bacteria and fungi in animals.

A still further object of this invention is to provide a process for the treatment of mange in animals, and particularly demodectic mange in dogs, which is more effective than treatments provided heretofore.

These and other objects are accomplished herein by a process which comprises topically applying a therapeutically effective amount of benzoyl peroxide to an animal.

DETAILED DESCRIPTION OF THE INVENTION

Benzoyl peroxide is a well-known chemical represented by the structural formula:

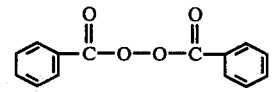

It is a colorless, odorless, tasteless, crystalline solid which is stable at ordinary room temperature but which is flammable and capable of exploding when confined and subject to grinding, heat or flame. Benzoyl peroxide is a powerful oxidizing agent, and is often used in polymer chemistry as a free-radical generating catalyst. Recently, it has been used as a keratolytic and antibacterial agent in the treatment of acne and seborrhea in humans. In this respect, attention is particularly invited to U.S. Pat. No. 3,535,422 and U.S. Pat. No. 3,530,217.

It has been surprisingly discovered herein that benzoyl peroxide is an overwhelmingly effective therapeutic agent for the treatment of microbial skin infections in animals. More particularly, benzoyl peroxide has been found to be especially effective against skin infections caused by parasites, bacteria and fungal pathogens in animals.

Typically, parasitic skin infections which are contemplated to be within the scope of the process of the present invention are generally those caused by acarids. More specifically, skin infections which are caused by acarids and which are contemplated to be treated by the process herein include for example, mange, caused by burrowing mites, such as Sarcoptes or Chorioptes; scabies, caused by scale-eating mites, such as Psoroptes; demodectic mange, caused by Demodex folliculorum; and related skin infections caused by other acarids.

Benzoyl peroxide has also been found herein to be effective in the treatment of bacterial infections in animals. Thus, bacterial infections which are caused by bacteria, such as staphylococcus aureus, and other gram positive organisms are among the skin infections contemplated to be treated by the process herein. Specific animal diseases which are caused by bacteria, and which are contemplated to be treated by the process of the present invention, include, for example, bacterial infections which may be secondary to an underlying dermatitis caused by parasites, such as in pyoderma or may be the primary problem such as in impetigo and folliculitis.

Furthermore, it has also been found that fungal infections in animals can be effectively treated with benzoyl peroxide. Fungal pathogens, such as Candida albicans and other yeastlike fungi and Trichophyton, are among the fungi which can be treated with benzoyl peroxide.

When applied in effective therapeutic parasiticidal dosages, the benzoyl peroxide has been found to be especially effective in the treatment of demodecosis and folliculitis in dogs. It has been found that benzoyl peroxide has an unusual ability to increase the cell turnover within hair follicles, thereby inducing a follicular flush, and resulting in the evacuation of the parasites habitating therein. Thus the phrase "parasiticidal amount" used herein in intended to include not only that amount of benzoyl peroxide which may kill the parasites but also that amount which causes the evacuation of or other abandonment by the parasites from the animal.

Moreover, it has been found that not only does the benzoyl peroxide provide a complete remission of the disease, it does not cause any deleterious side effects and, in addition, possesses desirable anti-inflammatory qualities.

In accordance with the process of the present invention, the benzoyl peroxide is generally advantageously incorporated in a suitable inert carrier, and the resultant composition is topically applied to the infected animal. By "inert," it is intended to mean carrier materials which do not chemically react with the benzoyl peroxide at ambient temperature and pressure.

Thus, suitable inert carrier materials useful in the formulation of benzoyl peroxide therapeutic compositions used in the practice of this invention include any of those ingredients used in the preparation of alcohol or acetone gels, creams, ointments, lotions, soaps, shampoos, and the like. More particularly, ingredients traditionally employed in the preparation of such formulations include, for example, water and organic emollients, such as alcohols, fatty acids and esters thereof, oils and mixtures thereof. Preferred organic emollients include aliphatic alcohols, having from about 2 to about 20 carbon atoms, such as butyl alcohol, isobutyl alcohol, amyl alcohol, isoamyl alcohol, hexyl alcohol, isohexyl alcohol, and mixtures thereof. Essentially water-insoluble higher aliphatic alcohols, like cetyl alcohol and the like, are also within the scope of this invention. Glycols, such as ethylene glycol, propylene glycol, diethylene glycol, and glycerol (glycerin) and mixtures thereof, are also contemplated emollients herein. Suitable fatty acids and esters thereof which are useful emollients herein include, for example, fatty acids having from 12 to 20 carbon atoms, and esters thereof. More specifically, these include lauric acid, myristic acid, palmitic acid, stearic acid, and the like; ethyl laurate, isopropyl laurate, ethyl myristate, n-propyl palmitate, isopropyl palmitate, methyl palmitate, methyl stearate, ethyl stearate, isopropyl stearate, butyl stearate, isobutyl stearate, amyl stearate, isoamyl stearate, and the like, and mixtures thereof. Other ingredients which are commonly employed in these types of formulations and which may be employed in the benzoyl peroxide formulations used herein include emulsifiers, suspending agents, thickeners and detergents, like polyethylene glycol 1000 monostearate, sodium lauryl sulfate, polyoxyethylene lauryl ether, hydrated aluminum magnesium silicate, triethanolamine, sulfated fatty alcohols (Duponals), carboxypolymethylenes (Carbopols, B. F. Goodrich Co.), and the like. Buffering agents, such as citric acid, are also employed. Aluminum hydroxide and petrolatum are also useful materials in the preparation of gels herein. Mixtures of all of the above ingredients are obviously also comtemplated herein.

For the purposes of this invention, and owing to the ease with which the formulation may be applied to the animal, the benzoyl peroxide is preferably incorporated in a liquid shampoo formulation. Typical ingredients which are used in the formulation of shampoos include potassium hydroxide, sodium hydroxide, soaps, oils, like coconut oil, sulfonated caster oil, sulfonated olive oil, mineral oil, and any of the emulsifiers, detergents and suspending agents identified hereinabove and the like, and mixtures thereof Other ingredients having anti-fungal, anti-bacterial or other anti-microbial properties may also be included within the benzoyl peroxide formulations used in the practice of this invention. For example, a particularly preferred antimicrobial ingredient is sulfur, which can comprise from about 1 to about 25 percent by weight and preferably from about 1 to about 10 percent by weight of the total composition.

A particularly preferred shampoo formulation useful in the practice of the present invention comprises benzoyl peroxide, sodium lauryl sulfate, polyoxyethylene lauryl ether and water. A particularly preferred gel formulation useful in the practice of this invention comprises benzoyl peroxide, water, acetone, propylene glycol, triethanolamine, sulfated fatty alcohols, and carboxypolymethylenes.

The benzoyl peroxide compositions used in the practice of the present process are made by any conventional means. For example, the composition can be prepared by carefully and thoroughly blending the benzoyl peroxide, organic emollients, emulsifiers, etc., water and other constituents of the composition. Advantageously, the fluid medium in which the benzoyl peroxide is to be dispersed is first prepared by forming an emulsion of the aqueous and non-aqueous phases of the fluid medium. The benzoyl peroxide and other constituents, such as sulfur, are then added to the emulsion and thoroughly blended therewith to form the therapeutic composition. While any form of benzoyl peroxide may be used, it is preferred to employ high purity benzoyl peroxide in the form of relatively finely divided crystalline particles.

In the practice of the present invention, the benzoyl peroxide can be applied to the animal in any therapeutically effective antimicrobial amount. Factors which influence the amounts of benzoyl peroxide used in the practice of the present invention include, for example, the size of the host animal, the extent of the treatment, and the amount of benzoyl peroxide which can be uniformly dispersed in the inert carrier. With these considerations in mind, therapeutically effective parasiticidal, bacteriocidal and/or fungicidal amounts of benzoyl peroxide for the purposes of this invention include amounts ranging from about 1% to about 25% by weight of the total formulation in which the benzoyl peroxide is incorporated and eventually applied. Preferably, amounts of benzoyl peroxide in the range of from about 2.5% to about 10% of the total composition are employed.

Any conventional means of topically applying the benzoyl peroxide to the skin of the infected animal may be used. For example, when the benzoyl peroxide is used in a shampoo or other liquid type formulation, such as a lotion, the animal may be dipped into the composition, or bathed or showered with the composition, with thorough rubbing of the composition into the skin. If the benzoyl peroxide composition is in the form of a solid, such as a cream, gel, or ointment, it is simply thoroughly rubbed into the infected areas.

The extent of treatment generally involves daily use as a shampoo, allowing the lather to remain on the animal for five to ten minutes before rinsing, or as a gel, cream or other solid vehicle applied once a day. The shampoo is utilized for more generalized disease, while the gel is applied to more localized areas. Treatment may be decreased to once or twice weekly as improvement occurs, and treatment may last for many weeks or months, depending upon the disease and its severity.

In order that those skilled in the art may better understand how to practice the present invention, the following examples are given, by way of illustration, and not by way of limitation:

EXAMPLE 1

A shampoo formulation comprising about 3.9% by weight of a 70% by weight benzoyl peroxide in water solution (Ludicol, Novadel-Agene Corp.), about 50% by weight sodium lauryl sulfate (Sipon LS/B, shampoo base), about 6% by weight polyoxyethylene lauryl ether (Macol LA-12), about 2.5% by weight hydrated aluminum magnesium silicate, (Veegum K, R. T. Vanderbilt Co.), about 1.0% by weight methylcellulose (Methocel E, 417 Premium, Dow Chemical Co.), about 0.21% by weight citric acid, and about 35.6% by weight distilled water, is applied to a 1 year old dog (German Shepherd) afflicted with demodectic mange (localized squamous form). After bi-weekly shampoo treatments over a period of approximately one month, the dog is in complete remission without deleterious side effects.

EXAMPLE 2

After having been previously treated with Ronnel (O,O-dimethyl O-(2,4,5-trichlorophenyl) phosphorothioate) without success, a 7 month old dog (mixed breed), suffering from generalized demodecosis, is treated with the same benzoyl peroxide shampoo formulation as in Example 1. After 20 topical shampoo treatments over a period of 3 months, the disease is completely remitted with continuous coat regrowth.

EXAMPLE 3

After having been previously treated with Ronnel (O,O-dimethyl O-(2,4,5-trichlorophenyl) phosphorothioate) without success, a 6 month old dog (Beagle) suffering from demodecosis (localized squamous form) is treated with the same benzoyl peroxide shampoo formulation as in Example 1. After five different topical shampoo treatments, the disease is completely remitted, with no side effects, and complete coat regrowth over the previously infected areas is observed.

EXAMPLE 4

A 2 year old Doberman Pinscher with 10 lesions of folliculitis is treated with the same benzoyl peroxide shampoo formulation as in Example 1 once weekly over a period of two weeks (i.e., a total of two shampoos). After the second weekly shampoo, the animal is completely cured.

EXAMPLE 5

A 5 month old German Shepherd with K-9 generalized impetigo is topically treated with the same benzoyl peroxide shampoo formulation as in Example 1 twice over a four-day period. This treatment is augmented with four daily applications of benzoyl peroxide acetone gel, applied directly to the lesions. The acetone gel comprises 7.85% by weight benzoyl peroxide (Lucidol, 70% benzoyl peroxide in water), 76.65% by weight deionized water, 1.50% by weight Carbopol 940 (carboxypolymethylene, B. F. Goodrich Co.), 1.00% by weight triethanolamine, 5.00% by weight propylene glycol, 5.00% by weight acetone, and 3.00% by weight Duponal (WAQE) (mixture of sulfated fatty alcohols. After 4 days of the above treatment, the animal is completely cured.

Obviously, other modifications and variations of the present invention are possible in the light of the above teachings. It is therefore to be understood that changes may be made in the particular embodiments of this invention which are within the full intended scope of the invention as defined by the appended claims.

What is claimed is:

1. A process for treating a skin infection, caused by an acarid-parasite, in an animal comprising topically applying a therapeutically effective parasiticidal amount of benzoyl peroxide to said animal.

2. The process of claim 1 wherein said benzoyl peroxide is incorporated in an inert carrier.

3. The process of claim 2 wherein said inert carrier is selected from the group consisting of a shampoo, a lotion, an ointment, a cream and a gel.

4. The process of claim 2 wherein said benzoyl peroxide comprises from about 1 to about 25 percent by weight of the total composition.

5. The process of claim 2 wherein said benzoyl peroxide comprises from about 2.5 to about 10 percent by weight of the total composition.

6. The process of claim 3 wherein said benzoyl peroxide comprises from about 1 to about 25 percent by weight of the total composition.

7. The process of claim 3 wherein said benzoyl peroxide comprises from about 2.5 to about 10 percent by weight of the total composition.

8. The process of claim 7 wherein said inert carrier is a shampoo.

9. The process of claim 7 wherein said inert carrier is a gel.

10. The process of claim 1 wherein said animal is afflicted with mange.

11. The process of claim 1 wherein said animal is afflicted with demodectic mange.

12. A process for treating a skin infection, caused by an acarid-parasite, in an animal comprising topically applying a therapeutically effective parasiticidal amount of benzoyl peroxide to an animal infested with said acarid-parasite.

13. The process of claim 12 wherein said animal is afflicted with mange.

14. The process of claim 12 wherein said animal is afflicted with demodectic mange.

15. The process of claim 12 wherein said benzoyl peroxide is incorporated in an inert carrier.

16. The process of claim 14 wherein said animal is a dog.

17. The process of claim 15 wherein said inert carrier is selected from the group consisting of a shampoo, a lotion, an ointment, a cream and a gel.

18. The process of claim 17 wherein said benzoyl peroxide comprises from about 1 to about 25 percent by weight of the total composition.

19. The process of claim 18 wherein said benzoyl peroxide comprises from about 2.5 to about 10 percent by weight of the total composition.

20. The process of claim 19 wherein said inert carrier is a shampoo comprising water, sodium lauryl sulfate and polyoxyethylene lauryl ether.

21. A process for treating a skin infection, caused by an acarid-parasite, in an animal comprising topically applying a therapeutically effective amount of benzoyl peroxide in a shampoo carrier to an animal afflicted with mange.

22. The process of claim 21 wherein said mange is demodectic mange.

23. The process of claim 22 wherein said animal is a dog.

24. The process of claim 21 wherein the benzoyl peroxide comprises from about 1 to about 25 percent by weight of the total shampoo composition.

25. The process of claim 24 wherein said benzoyl peroxide comprises from about 2.5 to about 10 percent by weight of the total shampoo composition.

26. The process of claim 25 wherein said shampoo carrier comprises water, sodium lauryl sulfate and polyoxyethylene lauryl ether.

27. A process for treating a skin infection, caused by an acarid-parasite, in an animal comprising topically applying a therapeutically effective amount of benzoyl peroxide in an inert carrier selected from the group consisting of a lotion, an ointment, a cream and a gel to an animal afflicted with mange.

28. The process of claim 27 wherein said mange is demodectic mange.

29. The process of claim 28 wherein said animal is a dog.

30. The process of claim 27 wherein the benzoyl peroxide comprises from about 1 to about 25 percent by weight of the total benzoyl peroxide and inert carrier composition.

31. The process of claim 30 wherein said benzoyl peroxide comprises from about 2.5 to about 10 percent by weight of the total benzoyl peroxide and inert carrier composition.

* * * * *